dix Autolite Corporation,
Fostoria, Ohio

[21] Appl. No.: 885,423

[22] Filed: Mar. 13, 1978

[51] Int. Cl.² .................. C23G 1/02; G01N 27/58
[52] U.S. Cl. ........................... 204/195 S; 134/41;
252/472
[58] Field of Search ..................... 204/15, 195 S;
123/119 E; 60/276; 252/472; 134/41

[56]         References Cited
         U.S. PATENT DOCUMENTS

| 3,514,377 | 5/1970 | Spacil et al. | 204/1 T |
| 3,699,032 | 10/1972 | Rapp | 204/195 S |
| 3,978,006 | 8/1976 | Topp et al. | 252/477 R |

United States Patent [19]
Davis et al.

[11] 4,136,000
[45] Jan. 23, 1979

[54] PROCESS FOR PRODUCING IMPROVED SOLID ELECTROLYTE OXYGEN GAS SENSORS

[75] Inventors: Donald C. Davis; Donald J. Romine, both of Fostoria; Phillip R. Woodruff, Tiffin, all of Ohio; James D. Bode, Royal Oak, Mich.; Tseng Y. Tien, Ann Arbor, Mich.; Ching T. Young, Troy, Mich.

[73] Assignee: Bendix Autolite Corporation, Fostoria, Ohio

FOREIGN PATENT DOCUMENTS

| 2433158 | 2/1975 | Fed. Rep. of Germany | 204/195 S |
| 975730 | 11/1964 | United Kingdom | 252/413 |

OTHER PUBLICATIONS

J. E. Bauerle, J. Phys. Chem. Soilds, pp. 2657-2670, vol. 30, (1969).

Primary Examiner—G. L. Kaplan
Attorney, Agent, or Firm—William G. Kratz; Raymond J. Eifler

[57]              ABSTRACT

An oxygen gas sensor having a solid electrolyte oxygen gas sensor element, with an inner conductive catalyst electrode on the interior surface and an outer conductive catalyst electrode on the exterior surface thereof, which has a high voltage output and lower internal resistance is produced by chemically activating said inner conductive catalyst electrode with an inorganic acid or an acid salt. By also subjecting said outer conductive catalyst electrode to a direct current activation under a reducing atmosphere, even more improved properties, such as fast switching response, are achieved.

21 Claims, No Drawings

PROCESS FOR PRODUCING IMPROVED SOLID ELECTROLYTE OXYGEN GAS SENSORS

BACKGROUND OF THE INVENTION

Oxygen gas sensors are known for use in measuring the oxygen content of an exhaust gas, such as in automobiles, to regulate the efficiency of an engine by varying the air to fuel ratio. One type of such an oxygen gas sensor has a solid electrolyte body in the general shape of a thimble, the solid electrolyte generally comprising a stabilized zirconium dioxide material, with electrodes formed on both the interior and exterior surfaces of the sensor element, the electrodes normally being formed of a catalytic material such as platinum. With the inner electrode exposed to a reference gas such as air, and the outer electrode exposed to the exhaust gas, the oxygen content of the exhaust gas can be measured to determine and regulate the air-fuel ratio of the gas mixture inlet to the engine. The voltage output of such zirconium dioxide sensors normally produce a voltage output the magnitude of which depends upon the oxygen partial pressure in the exhaust gas in which the sensor is immersed. Typically, such sensors, at exhaust temperatures above 350° C., should produce a voltage of about 900 millivolts in an exhaust gas richer than stoichiometry and about 50 millivolts in an exhaust gas leaner than stoichiometry. It has been found, however, that instead of the supposed 900 millivolts to 50 millivolts range, the output ranges of such sensors often would be as low as 0–400 millivolts in the rich gas phase and a negative 200–600 millivolts in the lean phase. The negative voltages occurred most frequently during low exhaust gas temperatures (350° C. or below) and tended to fall into more negative range with increased use.

In addition, the switching time or time required for the sensor to detect a change from rich to lean or lean to rich exhaust gas compositions must be as low as possible, preferably below about a half second (500 milliseconds), again especially during low temperature operation (about 350° C.) such as during engine warm-up.

The internal resistance of the sensor is a further factor which must be controlled since a low internal resistance will allow the sensor to sink or source more useful current from the monitoring system that is being used for determining the oxygen content of the exhaust gas.

The present process provides for the preparation of an oxygen gas sensor element which evidences these improved properties, a high positive voltage output, a fast switching time response and a low internal resistance.

SUMMARY OF THE INVENTION

An oxygen gas sensor element having a high positive voltage output, fast switching response and low internal resistance, the element comprising a solid electrolyte body, such as stabilized zirconium dioxide, and having an inner conductive catalyst electrode on the interior surface thereof for contact with a reference gas and an outer conductive catalyst electrode on the exterior surface thereof for exposure to the exhaust gas, is produced by chemically activating the inner conductive catalyst electrode with an inorganic acid or an acid salt. Further improvement is achieved by subjecting the outer conductive catalyst electrode to a reducing atmosphere and elevated temperature and applying a direct current to the sensor element under these conditions for a period of time and then maintaining these conditions for a recovery period after cessation of said current.

DESCRIPTION OF THE INVENTION

A gas sensor and improved gas sensor solid electrolyte sensing element are produced which have high positive voltage, fast switching response and low internal resistance. Undesirable reduction of positive voltage output is prevented, the generation of large negative voltages (greater than about −50 mv), is eliminated, and decreased internal resistance is achieved by the present process.

The gas sensor element is in the general shape of a closed tubular member, thimble-like, with the sensor body formed of a solid electrolyte material such as stabilized zirconium dioxide. This general shape of the electrolyte body is known in the art, as well as the solid electrolyte usable. The thimble-like shape of such sensor element, having a shoulder at the open end thereof, is illustrated in U.S. Pat. No. 3,978,006 and other existing publications, which also describe various solid electrolyte materials useful in forming such sensor elements, such as stabilized zirconium dioxide. The preferred composition for forming the solid electrolyte body is a mixture of zirconium dioxide and stabilizing materials such as calcium oxide or yttrium oxide.

To the interior surface of the electrolyte body, an inner electrode of conductive catalyst material is applied, such as by the coating of the surface with a platinum paste with or without a glass frit or other high temperature-resistance bonding material. This paste coating covers the interior surface of the closed terminal end and extends to the shoulder of the electrolyte body. This combination is then fired at a temperature of 600°–1000° C. or higher, as is known in the art, for a sufficient period of time to convert the platinum paste to an electrically conductive inner electrode.

A glass frit or other bonding agent, when used, while providing excellent adherence of the catalytic electrode to the interior surface of the solid electrolyte body, has an effect of increasing the internal electrical resistance of the sensor, and also reducing the positive output voltage of the sensor when the external surface thereof is exposed to a rich atmosphere and a negative voltage output when the external surface thereof is exposed to a lean atmosphere In the present process, the conductive catalyst electrode on the interior surface of the solid electrolyte body is subjected to a chemical activation treatment to improve the voltage output and to reduce the internal resistance of the sensor element. The treatment of the inner conductive catalyst electrode is by contact of the surface thereof with a solution of an inorganic acid or an acid salt. Aqueous solutions of an inorganic acid, such as hydrochloric acid, sulfuric acid, nitric acid, phosphoric acid, hydrofluoric acid and chloroplatinic acid are preferred, while acid salts such as ammonium chloride, hydroxylamine hydrochloride, ammonium chloroplatinate or the like, are also usable.

In treating the conductive catalyst electrode with an aqueous acidic or acid salt solution, the electrode may be contacted with the solution and the same held in contact for a period of time before removing the solution and rinsing, or the electrode in contact with the aqueous solution may be heated to evaporate solvent from the solution and then heated further to elevated temperatures in the range of up to 1200° C.

The chemical activation treatment is believed to remove or alter any film or coating which covers the surface of the inner conductive electrode or of the zirconia electrolyte, and results in a high voltage output in the positive range as well as a significant reduction in the internal resistance of the solid electrolyte body. This chemical activation treatment does not, however, appear to significantly reduce the response time required for switching from rich to lean gas composition readings. Current activation of the outer electrode, in conjunction with this inner electrode chemical activation, has been found to produce a significantly superior oxygen sensor element having even higher voltage output, exceptionally fast switching response and a low internal resistance.

In the current activation of the outer electrode, the conductive catalyst electrode coating on the exterior surface of the sensor element is subjected to an elevated temperature and a reducing atmosphere, while a direct current is applied to the sensor element with the outer electrode as a cathode and the inner electrode as an anode. After cessation of the current, the sensor element is maintained at the elevated temperature for a period of time for recovery.

The current activation of the outer conductive catalyst electrode is described in detail in the copending application of three of the inventors herein named, Ching T. Young, James D. Bode and Tseng Y. Tien, Ser. No. 854,875 filed Nov. 25, 1977, entitled "Process for Producing a Solid Electrolyte Oxygen Gas Sensor" copending herewith, the contents of said application being incorporated by reference herein. As described in said copending application, the conductive catalyst electrode is subjected to a reducing atmosphere and heated to a temperature in excess of about 500° C. While these conditions are present, a direct current is applied to the sensor element with the outer electrode acting as a cathode, the current density being between 5–1000 milliamperes per square centimeter of the planar surface of the outer electrode, for a period of time of about 2–30 minutes. After cessation of the current, the outer electrode is maintained at the elevated temperature and preferably in the presence of the reducing gas for a period of time for recovery.

The reducing atmosphere during the current activation is preferably carbon monoxide, with some moisture content, although hydrogen and rich exhaust gas mixtures and the like may also be used, as well as mixtures of the reducing gas with inert gases provided that the atmosphere is nonoxidizing. The elevated temperature to which the conductive catalyst coating is exposed is between about 500°–1200° C. with a temperature of between 700°–900° C. being preferred. While at these conditions, a direct current is applied to the sensor element, with the outer electrode as a cathode and the inner electrode as an anode. The current is applied at a current density of between 5–1000 milliamperes per square centimeter of the planar surface area of the outer conductive catalyst electrode, and the current is applied for a period of time of between about 2 to 30 minutes. After cessation of the current, a recovery time of about 3–10 minutes is required, with the conductive catalyst electrode maintained at said elevated temperature.

With respect to the present process, it has been found that provided the conductive catalyst electrode on the interior surface of the solid electrolyte body is subjected to a chemical activation step, the conductive catalyst electrode on the exterior surface is subjected to the current activation step, the order of such processing is immaterial, with either step being usable first.

The following examples further illustrate the present invention. In these examples, the testing of thimbles, as sensor elements, to determine their performance in terms of voltage output under rich and lean conditions, the switching response to gas variation and their internal resistance, was made by inserting the thimbles into protective housings with conductive leads connected to the inner and outer electrodes to form sensors. The tests were conducted at 350° C. and at 800° C.

The sensor performance tests were conducted by inserting the sensors into a cylindrical metal tube and exposing them to oxidizing and reducing gaseous atmospheres within the tube through use of a gas burner adjustable to produce such atmospheres. Sensors placed in the desired positions in the tube were heated to testing temperature and the voltage output measured using a volt meter. The output was also connected to an oscilloscope to measure the speed of response of the sensor when the burner flame is changed from rich to lean and from lean to rich. A routine test consisted of setting the flame to rich condition, measuring the voltage output of the sensor, switching the flame suddenly to lean condition, triggering the oscilloscope sweep at the same time to record the rich to lean switch of the sensor, switching the flame suddenly back to rich condition, again triggering the oscilloscope to record the sensor output change, and finally adjusting the flame to a lean condition and measuring the sensor output voltage. The switching time is defined as the time period required for the output voltage, as recorded on the oscilloscope, to sweep between 600 and 300 millivolts. When the sensor output voltage under rich gas condition is less than 600 millivolts, the switching response time is not determinable (n/d) according to the criteria used for this switching response measurement. Rich voltage output measurements were then made with different known values of shunting resistance across the sensor terminals. These measurements provided data for calculating the internal resistance of the sensors.

Where current activation was effected, the thimbles, as sensors in a protective housing and with conductive leads, were inserted into a manifold, with the exterior surface of the sensor element thereof having the outer conductive catalyst electrode thereon exposed to a reducing atmosphere (0.5% CO at a flow rate of 710 $cm^3$/min.) at a temperature of 850° C. The reducing atmosphere was allowed to pick up some moisture by bubbling it through water before it was admitted to the manifold. The sensor was then subjected to a direct current, with the outer electrode acting as a cathode, for 10 minutes. The direct current charge was applied at a current density of 150 milliamperes/$cm^2$ of outer electrode planar surface. The direct current was stopped and the sensor element allowed a recovery time of 8 minutes at said temperature and with the outer electrode in said reducing atmosphere.

A series of gas sensor electrolyte body thimbles were prepared, for use in the following examples, from ball-milled zirconia, yttria and alumina in a ratio of 80%, 14% and 6% by weight respectively, by isostatically pressing the same in the desired thimble shape and firing at high temperature.

EXAMPLE I

Five of the series of electrolyte body thimbles (12-9, 12-16, 12-13, 12-20 and 32-9) had an inner electrode applied to the inner surface thereof by coating the inner surface with a platinum suspension containing a vitrifying glass for bonding purposes. The thimble with its inner electrode was then heated in an oxidizing atmosphere to burn off the organic constituents of the suspension and bond the platinum to the zirconia surface. The external platinum catalyst electrode was next applied to the outer surface of the thimble by known thermal vapor deposition. A porous ceramic coating was applied over the external catalyst layer for protection. The thimbles were then formed into sensors and tested as to voltage output, switching response and internal resistance, as hereinbefore described. The results of the tests are listed in Table I under the designation "No Treatment."

The thimbles were then subjected to chemical activation by applying to the inner surface thereof 0.1 cc of a 2N (2 gram equivalent per liter of solution) of an aqueous solution of an inorganic acid or acid salt. For 12-9, a chloroplatinic acid solution was used; for 12-16, a hydrochloric acid solution; for 12-13, a nitric acid solution; for 12-20, a sulfuric acid solution; and for 32-9, an ammonium chloride solution. The sensors were heated in an oven to 105° C. to evaporate water from the aqueous solution and then heated to 800° C. for a 10 minute period. These sensors were then again tested as to voltage output, switching response and internal resistance. The results of these tests are listed in Table I under the heading "After Chemical Activation." After this testing, the sensors were subjected to the current activation as hereinbefore described. Following current activation, sensors were tested a final time as to voltage output, switching response and internal resistance. The results of the final testing are listed in Table I under the heading "After Chemical Activation and Current Activation."

EXAMPLE II

Another four of the series of electrolyte body thimbles (29-4, 29-17, 29-1 and 29-16) had an inner electrode applied to the inner surface thereof by coating the inner surface with a platinum metal suspension without any frit or glass present in the suspension. The thimble and inner electrode were then heated in an oxidizing atmosphere for a period of time, during which the organic constituents in the suspension were burned off and the platinum bonded to the zirconia surface. The external catalyst layer was next applied to the outer surface of the thimble by known thermal vapor deposition. A porous ceramic coating was applied over the external catalyst layer for protection. These thimbles were then formed into sensors and two of the sensors, 29-17 and 29-26, were tested, as hereinbefore described, to determine voltage output, switching response and internal resistance. The results of the test are listed in Table II under the designation "No Treatment." The other two sensors, 29-4 and 29-1, were not subjected to testing at this time. The four sensors were next subjected to a current activation treatment, as hereinbefore described, and, following the current activation treatment, the sensors were again tested as to voltage output, switching response and internal resistance. The results of these tests are listed in Table II under the heading "After Current Activation." As shown by these test results, the current activation improved the switching response of the sensors with or without performance testing prior to the current activation treatment.

Two of the sensors, 29-1 and 29-6, were not improved as much as desired by the current activation treatment above, and were subjected to chemical activation. Sensor 29-1 had applied to its inner thimble surface an aqueous chloroplatinic acid solution (0.1 cc of 2N solution)

TABLE I

| Sensor | Treatment | 350° Testing | | | | | 800° C Testing | | | | |
| | | Voltage Output | | Switching Response | | Internal Resistance | Voltage Output | | Switching Response | | Internal Resistance |
| | | Rich (mv) | Lean (mv) | RL (ms) | LR (ms) | tance (kΩ) | Rich (mv) | Lean (mv) | RL (ms) | LR (ms) | tance (Ω) |
|---|---|---|---|---|---|---|---|---|---|---|---|
| 12-9 | No Treatment | 246 | −408 | n/d | n/d | 318 | 816 | 75 | 30 | 110 | 241 |
| 12-16 | No Treatment | 327 | −339 | n/d | n/d | 425 | 807 | 62 | 25 | 100 | 237 |
| 12-13 | No Treatment | 260 | −250 | n/d | n/d | 599 | 812 | 71 | 25 | 100 | 91 |
| 12-20 | No Treatment | 248 | −270 | n/d | n/d | 794 | 740 | 48 | 20 | 130 | 288 |
| 32-9 | No Treatment | 206 | −330 | n/d | n/d | 289 | 813 | 43 | 25 | 70 | 138 |
| | After Chemical Activation | | | | | | | | | | |
| 12-9 | (H$_2$PtCl$_6$) | 899 | 50 | 16,400 | 80 | 22 | 802 | 85 | 55 | 90 | 53 |
| 12-16 | (HCl) | 935 | 75 | 11,000 | 50 | 20 | 800 | 90 | 30 | 55 | 46 |
| 12-13 | (HNO$_3$) | 767 | 124 | 16,700 | 100 | 135 | 842 | 85 | 70 | 80 | 114 |
| 12-20 | (H$_2$SO$_4$) | 885 | 78 | 14,200 | 85 | 53 | 822 | 68 | 35 | 85 | 99 |
| 32-9 | (NH$_4$Cl) | 819 | 64 | 5,100 | 150 | 23 | 829 | 48 | 15 | 130 | 71 |
| | After Chemical Activation and Current Activation | | | | | | | | | | |
| 12-9 | (H$_2$PtCl$_6$) | 988 | 38 | 90 | 40 | 5 | 845 | 82 | 30 | 25 | 38 |
| 12-16 | (HCl) | 964 | 30 | 100 | 50 | 7 | 859 | 86 | 25 | 25 | 34 |
| 12-13 | (HNO$_3$) | 895 | −1 | 70 | 70 | 49 | 840 | 62 | 35 | 45 | 55 |
| 12-20 | (H$_2$SO$_4$) | 946 | 43 | 110 | 70 | 40 | 842 | 62 | 30 | 30 | 62 |
| 32-9 | (NH$_4$Cl) | 969 | 37 | 80 | 45 | 7 | 835 | 61 | 15 | 20 | 11 |

As seen by the results listed in Table I, the chemical activation step using various inorganic acids and acid salts increases the voltage output of the sensor elements and decreases the internal resistance thereof, while a dual treatment of chemical activation and current activation additionally improves these properties while also reducing significantly the switching response time.

and sensor 29-6 had applied to its inner thimble surface an aqueous hydrochloric acid solution (0.1 cc of 2N solution). These two sensors were finally tested, as hereinbefore described, as to voltage output, switching response and internal resistance. The results of the final testing is listed in Table II under the heading "After Current Activation and Chemical Activation."

TABLE II

| | 350° C Testing | | | | 800° C Testing | | | |
| | Voltage Output | | Switching Response | | Internal Resistance | Voltage Output | | Switching Response | | Internal Resistance |
| | Rich | Lean | RL | LR | tance | Rich | Lean | RL | LR | tance |

TABLE II-continued

| Sensor | (mv) | (mv) | (ms) | (ms) | (kΩ) | (mv) | (mv) | (ms) | (ms) | (Ω) |
|---|---|---|---|---|---|---|---|---|---|---|
| | | | | | No Treatment | | | | | |
| 29-4 | No | Test | | | | No | Test | | | |
| 29-17 | 948 | 65 | 2,400 | 60 | 20 | 841 | 73 | 30 | 45 | 22 |
| 29-1 | No | Test | | | | No | Test | | | |
| 29-26 | 914 | 33 | 1,000 | 60 | 55 | 848 | 61 | 45 | 40 | 43 |
| | | | | After Current Activation | | | | | | |
| 29-4 | 960 | 41 | 120 | 50 | 31 | 843 | 67 | 35 | 25 | 12 |
| 29-17 | 971 | 47 | 150 | 50 | 29 | 842 | 62 | 40 | 35 | 11 |
| 29-1 | 848 | 20 | 210 | 90 | 108 | 816 | 64 | 55 | 40 | 54 |
| 29-26 | 725 | −90 | 65 | 80 | 113 | 830 | 63 | 35 | 35 | 40 |
| | | After Current Activation and Chemical Activation | | | | | | | | |
| 29-1 (H$_2$PtCl$_6$) | 974 | 20 | 200 | 70 | 24 | 815 | 62 | 35 | 30 | 12 |
| 29-26 (HCl) | 942 | 10 | 90 | 40 | 17 | 826 | 50 | 40 | 35 | 15 |

As shown by the test results in Table II, the chemical activation further improved the sensor performance with increased voltage output at 350° C. and reduced internal resistance both at 350° C. and 800° C.

EXAMPLE III

Four further electrolyte body thimbles of the series (12-4, 12-5, 12-7 and 12-8) had inner and outer catalytic electrodes applied thereto as such application was effected in Example I, and formed into sensors and tested as in Example I. The results of the tests are listed in Table III under the heading "No Treatment." Two of the sensors, 12-4 and 12-5, were then subjected to current activation as hereinbefore described. The other two sensors, 12-7 and 12-8, were chemically activated using chloroplatinic acid (as was 12-9 in Example I). The four sensors were again tested and the results of the tests are listed in Table III under the heading "Single Treatment." The two sensors, 12-4 and 12-5, were then subjected to the chemical activation treatment (as were 12-7 and 12-8 initially) while the other two sensors, 12-7 and 12-8, were then subjected to the current activation treatment (as were 12-4 and 12-5 initially). The four sensors were finally tested as to voltage output, switching response and internal resistance. The results of the final testing are listed in Table III under the heading "After Current Activation and Chemical Activation."

In Table III, the results indicate that the chemical activation improves voltage output and lowers the internal resistance of the sensor elements and that dual treatment is effective whether chemical activation is done before or following current activation of the sensor elements.

EXAMPLE IV

An additional three of the series of electrolyte body thimbles (26-5, 26-6 and 26-8) had inner and outer catalytic electrodes applied as such application was effected in Example I, and formed into sensors and tested as in Example I. The results of the tests are listed in Table IV under the heading "No Treatment."

These thimbles were then removed from their housings and subjected to chemical activation by applying to the inner surface thereof 0.1 cc of a 2N aqueous solution of hydrochloric acid. The aqueous acidic solution was held in contact with the inner surface, and warmed to 50° C. for 30 minutes, and then removed and the inner surface rinsed with methanol.

After return to housings, the sensors were again tested, the results of these tests are listed under the heading "After Chemical Activation" in Table IV. These three sensors were then subjected to current activation, as hereinbefore described, and finally tested, with the results of the final tests listed in Table IV under

TABLE III

| | 350° C Testing | | | | | 800° C Testing | | | | |
|---|---|---|---|---|---|---|---|---|---|---|
| | Voltage Output | | Switching Response | | Internal Resistance | Voltage Output | | Switching Response | | Internal Resistance |
| Sensor | Rich (mv) | Lean (mv) | RL (ms) | LR (ms) | (kΩ) | Rich (mv) | Lean (mv) | RL (ms) | LR (ms) | (Ω) |
| | | | | | No Treatment | | | | | |
| 12-4 | 160 | −372 | n/d | n/d | 479 | 810 | 65 | 35 | 125 | 425 |
| 12-5 | −40 | −666 | n/d | n/d | 154 | 805 | 58 | 25 | 120 | 270 |
| 12-7 | 130 | −460 | n/d | n/d | 409 | 816 | 75 | 30 | 110 | 241 |
| 12-8 | 16 | −604 | n/d | n/d | 85 | 772 | 52 | 30 | 110 | 162 |
| | | | | | Single Treatment | | | | | |
| 12-4 | 640 | −40 | 180 | 280 | 308 | 829 | 47 | 15 | 45 | 357 |
| 12-5 | 695 | 18 | 120 | 135 | 202 | 831 | 54 | 20 | 35 | 109 |
| 12-7 | 935 | 65 | 13,800 | 50 | 17 | 790 | 78 | 35 | 75 | 59 |
| 12-8 | 905 | 70 | 19,600 | 70 | 15 | 793 | 67 | 45 | 70 | 184 |
| | | | After Current Activation and Chemical Activation | | | | | | | |
| 12-4 | 909 | −22 | 40 | 40 | 9 | 825 | 51 | 15 | 25 | 35 |
| 12-5 | 912 | 0 | 40 | 30 | 17 | 813 | 50 | 25 | 25 | 79 |
| 12-7 | 975 | 50 | 100 | 45 | 8 | 849 | 87 | 25 | 25 | 30 |
| 12-8 | 992 | 52 | 120 | 50 | 5 | 845 | 76 | 25 | 25 | 55 | the heading "After Chemical Activation and Current Activation."

TABLE IV

| | 350° C Testing | | | 800° C Testing | | |
|---|---|---|---|---|---|---|
| | Voltage Output | Switching Response | Internal Resis- | Voltage Output | Switching Response | Internal Resis- |

TABLE IV-continued

| Sensor | Rich (mv) | Lean (mv) | RL (ms) | LR (ms) | tance (kΩ) | Rich (mv) | Lean (mv) | RL (ms) | LR (ms) | tance (Ω) |
|---|---|---|---|---|---|---|---|---|---|---|
| | | | | | No Treatment | | | | | |
| 26-5 | 88 | −660 | n/d | n/d | 90 | 815 | 79 | 20 | 80 | 230 |
| 26-6 | 131 | −515 | n/d | n/d | 251 | 825 | 77 | 20 | 50 | 101 |
| 26-8 | 65 | −585 | n/d | n/d | 137 | 790 | 58 | 30 | 60 | 231 |
| | | | | After Chemical Activation | | | | | | |
| 26-5 | 854 | 25 | 7,800 | 40 | 62 | 833 | 65 | 20 | 50 | 70 |
| 26-6 | 890 | 70 | 6,900 | 60 | 52 | 830 | 68 | 30 | 50 | 88 |
| 26-8 | 906 | 90 | 7,300 | 110 | 42 | 824 | 57 | 30 | 60 | 97 |
| | | | After Current Activation and Chemical Activation | | | | | | | |
| 26-5 | 872 | 8 | 150 | 70 | 84 | 839 | 70 | 30 | 25 | 46 |
| 26-6 | 847 | 3 | 110 | 50 | 85 | 836 | 69 | 30 | 20 | 43 |
| 26-8 | 903 | 34 | 70 | 45 | 40 | 846 | 88 | 30 | 30 | |

The results in Table IV show that the chemical activation step can be effected without heating of the sensor element and inorganic acid in contact therewith.

We claim:

1. A process for producing an oxygen gas sensor element wherein the sensor element comprises a solid electrolyte body having an inner electrode of conductive catalyst material on the interior surface thereof, the exposed surface of said inner electrode being for exposure to a reference gas, and an outer electrode of conductive catalyst material on the exterior surface thereof for exposure to a gaseous mixture, the oxygen content of which is to be measured, comprising:
   contacting said inner conductive catalyst with an acidic reactant selected from the group consisting of inorganic acids and acid salts to chemically activate said electrode, whereby the voltage output of the sensor element is increased and the internal resistance decreased.

2. The process for producing an oxygen gas sensor element as defined in claim 1 wherein said acidic reactant is an inorganic acid selected from the group consisting of chloroplatinic acid, hydrochloric acid, sulfuric acid and nitric acid.

3. The process for producing an oxygen gas sensor element as defined in claim 1 wherein said acidic reactant is an acid salt.

4. The process for producing an oxygen gas sensor element as defined in claim 3 wherein said acid salt is selected from the group consisting of ammonium chloride and ammonium chloroplatinate.

5. The process for producing an oxygen gas sensor element as defined in claim 1 wherein said inner electrode comprises a platinum family metal catalyst.

6. The process for producing an oxygen gas sensor element as defined in claim 5 wherein said platinum family metal catalyst is bonded to said solid electrolyte body with a glass frit.

7. The process of producing an oxygen gas sensor element as defined in claim 1 wherein said sensor element is heated while said inner conductive catalyst electrode is in contact with the inorganic acidic reactant.

8. The oxygen gas sensor element produced according to the process of claim 1.

9. A process for producing an oxygen gas sensor element wherein the sensor element comprises a solid electrolyte body having an inner electrode of conductive catalyst material on the interior surface thereof, the exposed surface of said inner electrode being for exposure to a reference gas, and an outer electrode of conductive catalyst material on the exterior surface thereof for exposure to a gaseous mixture, the oxygen content of which is to be measured, comprising:
   (a) contacting said inner conductive catalyst electrode with an acidic reactant selected from the group consisting of inorganic acids and acid salts;
   (b) applying a direct current to said sensor element, with the outer electrode as a cathode, while subjecting the outer catalyst electrode to a reducing atmosphere at an elevated temperature; and
   (c) maintaining said outer electrode, after cessation of said current, at the elevated temperature for a period of time for recovery.

10. The process for producing an oxygen gas sensor element as defined in claim 9 wherein said contacting of the inner electrode with said acidic reactant is effected and thereafter the application of said direct current to the outer electrode is effected.

11. The process for producing an oxygen gas sensor element as defined in claim 9 wherein said application of the direct current to the outer electrode is effected and thereafter said contacting of the inner electrode with said acidic reactant is effected.

12. The process for producing an oxygen gas sensor element as defined in claim 9 wherein the conductive catalyst material of said electrodes comprises a platinum family metal catalyst.

13. The process for producing an oxygen gas sensor element as defined in claim 9 wherein said inner electrode comprises a layer of platinum bonded to said solid electrolyte body with a glass frit.

14. The process for producing an oxygen gas sensor element as defined in claim 9 wherein said acidic reactant is an inorganic acid selected from the group consisting of chloroplatinic acid, hydrochloric acid, sulfuric acid and nitric acid.

15. The process for producing an oxygen gas sensor element as defined in claim 9 wherein said acidic reactant is an acid salt.

16. The process for producing an oxygen gas sensor element as defined in claim 15 wherein said acid salt is selected from the group consisting of ammonium chloride and ammonium chloroplatinate.

17. The process for producing an oxygen gas sensor element as defined in claim 9 wherein said direct current is applied while the sensor element is at an elevated temperature of between 500°–1200° C.

18. The process for producing an oxygen gas sensor element as defined in claim 9 wherein said direct current is applied at a current density of between 5–1000 milliamperes per square centimeter of the planar surface of said outer electrode.

19. The process for producing an oxygen gas sensor element as defined in claim 9 wherein said direct current is applied for a period of time of between 2–30 minutes.

20. The process for producing an oxygen gas sensor element as defined in claim 9 wherein said period of time for recovery is in excess of 3 minutes.

21. The oxygen gas sensor element produced according to the process of claim 9.

* * * * *